United States Patent
Braginsky et al.

(10) Patent No.: US 6,972,031 B1
(45) Date of Patent: Dec. 6, 2005

(54) EXTERIOR STENT AND ITS USE

(76) Inventors: Sidney Braginsky, 6 Stonywell Ct., Dix Hills, NY (US) 11746; Russell A. Houser, 1787 Verdite St., Livermore, CA (US) 94550

( * ) Notice: Subject to any disclaimer, the term of this patent is extended or adjusted under 35 U.S.C. 154(b) by 0 days.

(21) Appl. No.: 10/037,817

(22) Filed: Jan. 3, 2002

(51) Int. Cl.[7] .................................. A61F 2/06
(52) U.S. Cl. ..................... 623/1.15; 606/108
(58) Field of Search ............... 623/1.11–1.22; 606/108, 191–195, 198, 153–156, 213–215; 604/43, 93, 181, 257

(56) References Cited

U.S. PATENT DOCUMENTS 5,968,089 A * 10/1999 Krajicek ................ 623/1.15
6,030,395 A * 2/2000 Nash et al. ............. 606/153
6,554,856 B1 * 4/2003 Doorly et al. .......... 623/1.15

FOREIGN PATENT DOCUMENTS

GB      2 344 053      5/2000

* cited by examiner

Primary Examiner—Vy Bui
(74) Attorney, Agent, or Firm—John A. Monocello, III, Esq.; Cohen & Grigsby, P.C.

(57) ABSTRACT

A stent apparatus and its use is provided comprising a substantially tubular member with an inside surface and an outside surface; and a securing element for securing the tubular member to the exterior of a body lumen. The method for implanting the stent to the exterior of a body lumen comprises providing for an exterior stent, inserting the stent around a desired location on the exterior of the lumen, and providing for controlled expansion of the lumen such that it contacts the stent sufficiently to secure it to the lumen.

23 Claims, 1 Drawing Sheet

EXTERIOR STENT AND ITS USE

CROSS REFERENCES TO RELATED APPLICATIONS

This application claims the benefit of U.S. Provisional Application Ser. No. 60/259,052 filed on Dec. 29, 2000.

BACKGROUND OF THE INVENTION

Intralumenal grafting and stents are used to hold a body lumen open and enlarged. This involves the percutaneous insertion and placement by catheter of a cylindrical prosthetic device within a body lumen. Stents are used in the vascular system, respiratory, biliary and urinary tracts. Typically, they are composed of stainless steal springs, wire in a zigzag pattern or helically wound springs.

Intralumenal grafts create several potentially dangerous conditions. If the grafts are under expanded at their target location in the lumen or under sized for the lumen, they do not secure themselves properly and can migrate away from the location. An over expanded or oversized graft can rupture the lumen.

Balloon dilation has been used as an alternative or in conjunction with stents for relieving elastic vascular senses. This procedure has many disadvantages and limitations. Incompressible plaque is unaffected and the stretching can cause fissuring. Balloon dilations can also cause early restenosis due to the recoil of the body lumen.

SUMMARY OF THE INVENTION

The present invention is directed to a method and prosthesis that is capable of opening and enlarging body lumens from the exterior. The invention provides for external, atraumatic vessel support. The support may be made from a biologically inert material and may be reinforced with a layer consisting of a polymer or metallic braid, wrap or other pattern. It may be secured to the exterior of the lumen using an adhesive, protruding member, suture or a combination of these means.

The result of the use of the present invention is a larger and reinforced lumenal vessel diameter. This can increase blood flow for cardiovascular vessels. The present invention does not require the implanting of a foreign object into the body lumen.

DETAILED DESCRIPTION OF THE INVENTION

Figure 1:
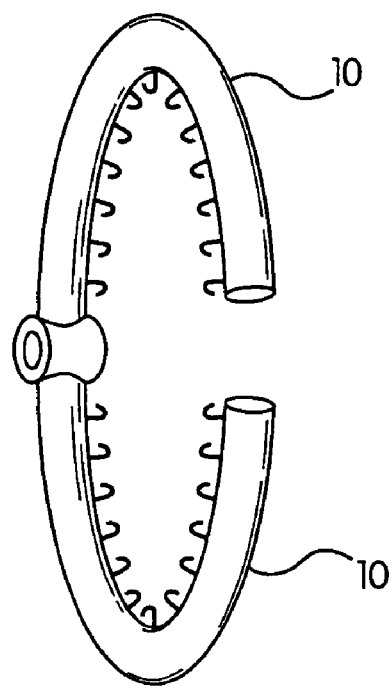
FIG. 1 is a depiction of the support with a hinge.

This support may comprise a single or multiple pieces. In FIG. 1 the single piece design would be constructed as two semi-cylindrical elements that are integrally connected at a hinge or flexible element. The two semi-cylindrical elements 10 are constructed to connect to each other opposite the hinge 20. They can latch or use some other method of connecting that will hold the device in a mostly tubular shape. However, the support does not have to provide complete circumferential contact. The design could offer sufficient reinforcement to the vessel with as little as 40% coverage and possibly less.

The interior side of the support (the side in contact with the lumen) may be made from a softer, compliant, more atraumatic material. The outer layer may be stronger and less compliant. The whole support may also be flexible.

The interior side may be coated or composed of a biologically inert adhesive. The adhesive is used to adhere to the exterior of the target body lumen. Alternatively, the support may be secured by penetrating barbs or hooks or reversible adhesive bonding between the lumen and support. Additionally, locking tabs or a ratchet system may be used to tighten and secure the support onto the lumen.

The device is constructed in different sizes to be able to approximate the size of the target lumen or is able to expand or contract to properly reach the lumen size.

The support may be made from expanded PTFE (ePtfe), woven Dacron or other suitable material. It may be made from biodegradable material, including but not limited to collagen, synthetic polymers such as polyglycolic acids, polylactids, polyhydroxybutyrates, polyhydroxyvaleriates, polydioxanons, modified starches, gelatins, modified celluloses, polyglycols, polyacrylic acids, polymethacrylic acids, natural or synthetic aliphatic or hydroxy polymer of lactic acid, glycolic acid or some combination of these or others.

Extrusion, molding, dip coating or a combination of these methods or other methods may be used to manufacture the support. The support may be made from a single piece and may have a porous or corrugated surface on one or both the exterior and interior sides.

The support may have holes or groves completely through it to provide the vessel with nutrients.

The support may be secured to the lumen wall by an adhesive such as cyanoacrylate, fibrin, fibrinogen, or some combination of these. However the adhesive is not limited to these. The adhesive could have a surface contact cure method such as UV light, heat or some combination.

During fabrication, the support can be annealed around an appropriately sized rod or mandrel, to increase radial strength as well as dimensional and geometric stability.

One or more layers of the support may be braided, woven, wrapped or other pattern. The support may have layers consisting of polymer, metal or a combination for surface texture and strength.

A method of use for the stent includes placing it around the exterior of the lumen and closing it into its cylindrical shape. The lumen is pushed against the interior of the stent where it comes into contact with the adhesive and sticks to the interior of the stent thereby enlarging and opening the lumen. The lumen is expanded to push against the stent by an angioplasty balloon or other similar device.

The support may be placed around a target lumen and ratcheted or compressed down to contact the lumen. The contact is sufficient when the lumen becomes secure to the support by the barbs or adhesive or other securing means. Alternatively, a PICA balloon catheter may be advanced within the lumen into place with the balloon positioned at the site of the external support. The balloon is then inflated causing the lumen to expand and come into contact with the interior side of the support bonding the lumen to the support. The balloon is then deflated and the catheter withdrawn.

Figure 2:
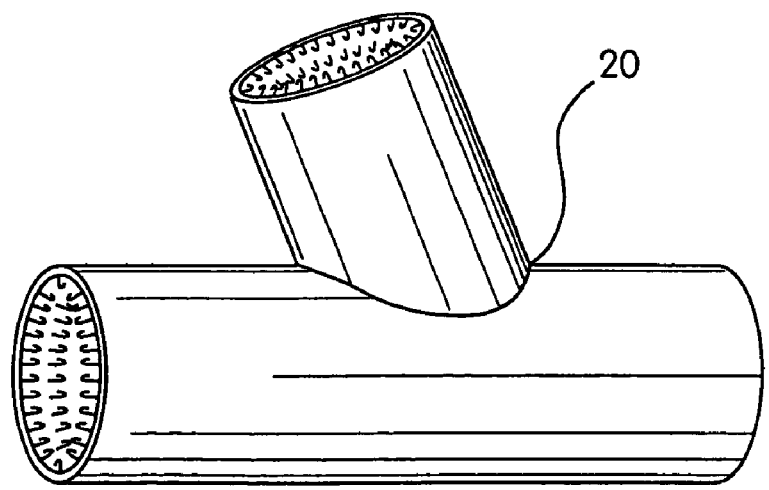
FIG. 2 is a depiction of a bifurcated support.

As shown in FIG. 2, the support may be bifurcated or more to provide for coverage of bifurcated lumens.

Accordingly, it should be readily appreciated that the exterior stent and the uses of the present invention has many practical applications. Additionally, although the preferred embodiment has been illustrated and described, it will be obvious to those skilled in the art that various modifications can be made without departing from the spirit and scope of this invention. Such modifications are to be considered as included in the following claims unless the claims expressly recite differently.

What is claimed is:

1. A method of supporting a body lumen comprising the steps of:
   a) providing a stent having an interior layer and an exterior layer, said interior layer having a securing means thereon;
   b) placing said stent around the exterior of a body lumen;
   c) expanding said lumen into contact with said securing means, thereby securing the lumen to the securing means.

2. A method of supporting a body lumen comprising the steps of:
   a) providing a stent having an interior layer and an exterior layer, said interior layer having a securing means thereon;
   b) placing said stent around the exterior of a body lumen;
   c) contacting the interior layer of said stent to said lumen, thereby securing the lumen to the securing means.

3. A method of support as in claim 1 or 2 wherein: the sent covers less than the total circumference of the lumen.

4. A method of support as in claim 1 or 2 wherein: the stent comprises a biologically inert material.

5. A method of support as in claim 4 wherein: the stent further comprises a shape-memory material.

6. A method of support as in claim 1 or 2 wherein: the stent comprises a biologically active material.

7. A method of support as in claim 1 or 2 wherein: the stent comprises resorbable material.

8. A method of support as in claim 1 or 2 wherein: the stent comprises a radioactive element for delivering radiation directly to the lumen.

9. A method as in claim 1 or 2 wherein: the stent is porous.

10. A method of support as in claim 1 or 2 wherein: the stent is a single unified member.

11. A method of support as in claim 1 or 2 wherein: the stent comprises at least two members flexibly joined together.

12. A method of support as in claim 1 or 2 wherein: the stent is bifurcated.

13. A method of support as in claim 1 or 2 wherein: the stent is further secured by a barb.

14. A method of support as in claim 1 or 2 wherein: the stent is secured by a hook.

15. A method of support as in claim 1 or 2 wherein: the stent is secured by an adhesive.

16. A method of support as in claim 1 or 2 wherein: the stent comprises a braided material.

17. A method of support as in claim 1 or 2 wherein; the support is substantially composed of resorbable material.

18. A method of support as in claim 1 or 2 wherein: the stent is further secured by sutures.

19. A method of support as in claim 1 or 2 further comprising the step of:
   locking the stent onto the lumen to prevent it from slipping.

20. A method of support as in claim 1 or 2 further comprising:
   applying a reinforcing layer for strengthening the stent.

21. The method of claim 2 wherein said step of contacting the interior layer of said stent to said lumen comprises ratcheting said stent.

22. The method of claim 2 wherein said step of contacting the interior layer of said stent to said lumen further comprises compressing said stent into said lumen.

23. The method of claim 1 wherein said step of expanding said lumen into contact with said securing means further comprises dilating said lumen with a balloon device.

* * * * *